(12) United States Patent
Kato et al.

(10) Patent No.: US 8,897,852 B2
(45) Date of Patent: Nov. 25, 2014

(54) BIOLOGICAL INFORMATION DETECTION DEVICE

(71) Applicants: Teruo Kato, Chiba (JP); Dai Terasawa, Chiba (JP); Hideki Okuda, Chiba (JP)

(72) Inventors: Teruo Kato, Chiba (JP); Dai Terasawa, Chiba (JP); Hideki Okuda, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 13/628,127

(22) Filed: Sep. 27, 2012

(65) Prior Publication Data

US 2013/0096411 A1   Apr. 18, 2013

(30) Foreign Application Priority Data

Oct. 13, 2011   (JP) ................................. 2011-225978

(51) Int. Cl.
| A61B 5/02 | (2006.01) |
| A61B 5/08 | (2006.01) |
| A61B 5/0408 | (2006.01) |
| A61B 5/00 | (2006.01) |
| A61B 5/024 | (2006.01) |
| A61B 5/0245 | (2006.01) |

(52) U.S. Cl.
CPC ............. A61B 5/0408 (2013.01); A61B 5/6831 (2013.01); *A61B 2560/0468* (2013.01); *A61B 5/0245* (2013.01); *A61B 5/04085* (2013.01); *A61B 5/02438* (2013.01)
USPC .......................................... 600/390; 600/509

(58) Field of Classification Search
CPC ............. A61B 5/0408; A61B 5/04085; A61B 5/6831; A61B 2560/0468
USPC .................................. 600/390, 509
See application file for complete search history.

(56) References Cited

U.S. PATENT DOCUMENTS

| 3,659,586 | A | * | 5/1972 | Johns et al. ................... 600/354 |
| 4,809,700 | A | * | 3/1989 | Castelli ......................... 600/384 |
| 5,491,474 | A | * | 2/1996 | Suni et al. ................ 340/870.31 |
| 6,272,365 | B1 | * | 8/2001 | Ronkainen et al. ........... 600/390 |
| 6,553,247 | B1 | * | 4/2003 | Rytky ........................... 600/386 |
| 6,600,942 | B2 | * | 7/2003 | Nissila et al. ................ 600/372 |
| 7,167,737 | B2 | * | 1/2007 | Fujii et al. ..................... 600/390 |
| 7,526,840 | B2 | | 5/2009 | Pernu et al. ..................... 24/265 |
| D603,521 | S | | 11/2009 | Lindberg et al. ............. D24/187 |
| 2009/0099472 | A1 | * | 4/2009 | Remmert et al. ............. 600/534 |
| 2010/0191090 | A1 | * | 7/2010 | Shin et al. ..................... 600/388 |

OTHER PUBLICATIONS

Patent Abstracts of Japan, Publication No. 02-299637, Publication Date Dec. 11, 1990.
Patent Abstracts of Japan, Publication No. 10-155753, Publication Date Jun. 16, 1998.
Patent Abstracts of Japan, Publication No. 2001-340311, Publication Date Dec. 11, 2001.
Patent Abstracts of Japan, Publication No. 2006-187615, Publication Date Jul. 20, 2006.

* cited by examiner

*Primary Examiner* — Lee S Cohen
(74) *Attorney, Agent, or Firm* — Adams & Wilks (57) ABSTRACT

A biological information detection device has a device main body and a biological signal detection portion formed integrally with the device main body. The biological signal detection portion has at least one electrode for contacting a biological surface of a human body. A fixing portion has an elastic strap and is configured to mount the device main body and the biological signal detection portion to the human body without the device main body and the biological signal detection portion being directly attached to the elastic strap. The fixing portion covers the device main body and the biological signal detection portion with the electrode being disposed in contact with the biological surface of the human body when the device main body and the biological signal detection portion are mounted to the human body.

18 Claims, 11 Drawing Sheets

BIOLOGICAL INFORMATION DETECTION DEVICE

BACKGROUND OF THE INVENTION

1. Field of the Invention

The present invention relates to a biological information detection device that detects a biological signal by installing an electrode on the biological surface of the human body.

2. Background Art

Among these kinds of biological information detection devices, there is, for example, a heartbeat measurement device that detects an electro-cardiac signal generated in association with a heartbeat, and measures a heart rate from the biological surface. As such a heartbeat measurement device, there is, for example, a device which includes a main body portion having a detection circuit board and the like built-in, and a strap for mounting the main body portion to the human body, the strap being provided with a pair of electrodes. The main body portion and the strap are provided with an electrical connection portion for electrically connecting a detection circuit board of the main body portion to an electrode of the strap.

Based on such a configuration, an electro-cardiac signal generated in association with a heartbeat is detected by bringing a pair of electrodes into contact with the chest (biological surface) of the human body, and the main body portion derives a heart rate on the basis of the detected electro-cardiac signal.

Further, among the heartbeat measurement devices, there is, for example, a device in which the main body portion is detachably provided to the strap from the viewpoint of maintenance such as cleaning of the strap. When the main body portion is mounted to the strap, the electrical connection portion provided to the strap and the electrical connection portion provided to the main body portion are mechanically connected to each other, and the detection circuit board and the electrode are electrically connected to each other (see, for example, Specification of U.S. Pat. No. 7,526,840 and U.S. Design Registration No. 603,521).

SUMMARY OF THE INVENTION

However, in the above-mentioned related art, since the main body portion and the electrode are formed detachably to each other, there is a problem that the detection performance of the heartbeat measurement device becomes unstable depending on the installation conditions of the electrical connection portion. In addition, there is a concern that the electrical connection portion is damaged by repeatedly performing attaching and detaching operations of the main body portion and the electrode.

Further, since the strap is provided with an electrode, an external force in the tensile direction is applied to the electrode and the electrical connection portion at all times, in a state where the heartbeat measurement device is installed on the human body. For this reason, there is a concern that the electrical connection portion provided to the strap and the electrical connection portion provided to the main body portion is mechanically separated from each other, and thus the electrical connection between the detection circuit board and the electrode are cut off. In addition to this, there is a concern that the electrode portion is exposed to a cleaning solution in association with cleaning of the strap at the time of maintenance, and thus that electrical parts such as the electrode and the electrical connection portion become damaged.

Consequently, the present invention is contrived in view of such circumstances, and an object thereof is to provide a biological information detection device capable of preventing defects from occurring in electrical parts such as the electrode and the electrical connection portion while securing good maintenance, and preventing the detection performance from becoming unstable.

According to an aspect of the present invention, there is provided a biological information detection device including: a device main body; a biological signal detection portion, formed integrally with the device main body, which has an electrode that comes into contact with a biological surface; and a fixing portion, formed so as to cover the device main body and the biological signal detection portion, which fixes the device main body and the biological signal detection portion to a human body.

According to such a configuration, since the device main body and the biological signal detection portion can be fixed to the human body in a state where the fixing portion and the biological signal detection portion including the electrode are separated from each other, it is possible to prevent an external force from being applied to the biological signal detection portion. In addition, the device main body and the biological signal detection portion can be separated from the fixing portion in a state where the device main body and the biological signal detection portion are formed integrally with each other. For this reason, it is possible to perform cleaning of a simple fixing portion while securing good maintenance, and to reliably prevent defects from occurring in electrical parts such as the electrode and the electrical connection portion.

In the biological information detection device according to the foregoing aspect, the device main body may be detachably provided to the fixing portion.

According to such a configuration, it is possible to easily perform positioning of the device main body with respect to the fixing portion, and to reliably prevent the device main body from falling off the fixing portion. For this reason, it is possible to provide a biological information detection device having good installation stability.

In the biological information detection device according to the foregoing aspect, the fixing portion may be configured such that at least an elastic strap and a non-elastic belt are connected to each other, and that the device main body is detachably provided to the belt.

In this case, the fixing portion may be configured such that at least an elastic strap and a hard connection member are connected to each other, and that the device main body is detachably provided to the connection member.

According to such a configuration, it is possible to increase adhesion of the biological information detection device to the human body using the strap. In addition, in the fixing portion, it is possible to prevent the portion to which the device main body is mounted from being deformed, and to reliably prevent the device main body from falling off the fixing portion.

In the biological information detection device according to the foregoing aspect, the biological signal detection portion may be formed from a conductive elastomer, and the conductive elastomer may serve as the electrode.

According to such a configuration, it is possible to easily elastically deform the biological signal detection portion, and to increase adhesion of the electrode to the biological surface. For this reason, it is possible to detect the biological signal with a higher degree of accuracy.

According to the present invention, since the device main body and the biological signal detection portion can be fixed to the human body in a state where the fixing portion and the biological signal detection portion including the electrode are separated from each other, it is possible to prevent an external force from being applied to the biological signal detection portion. In addition, the device main body and the biological signal detection portion can be separated from the fixing portion in a state where the device main body and the biological signal detection portion are formed integrally with each other. For this reason, it is possible to perform cleaning of a simple fixing portion while securing good maintenance, and to reliably prevent defects from occurring in electrical parts such as the electrode and the electrical connection portion.

DETAILED DESCRIPTION OF THE INVENTION

First Embodiment (Heartbeat Measurement Device)

Next, a first embodiment of the present invention will be described with reference to FIGS. 1 to 3.

Figure 1:
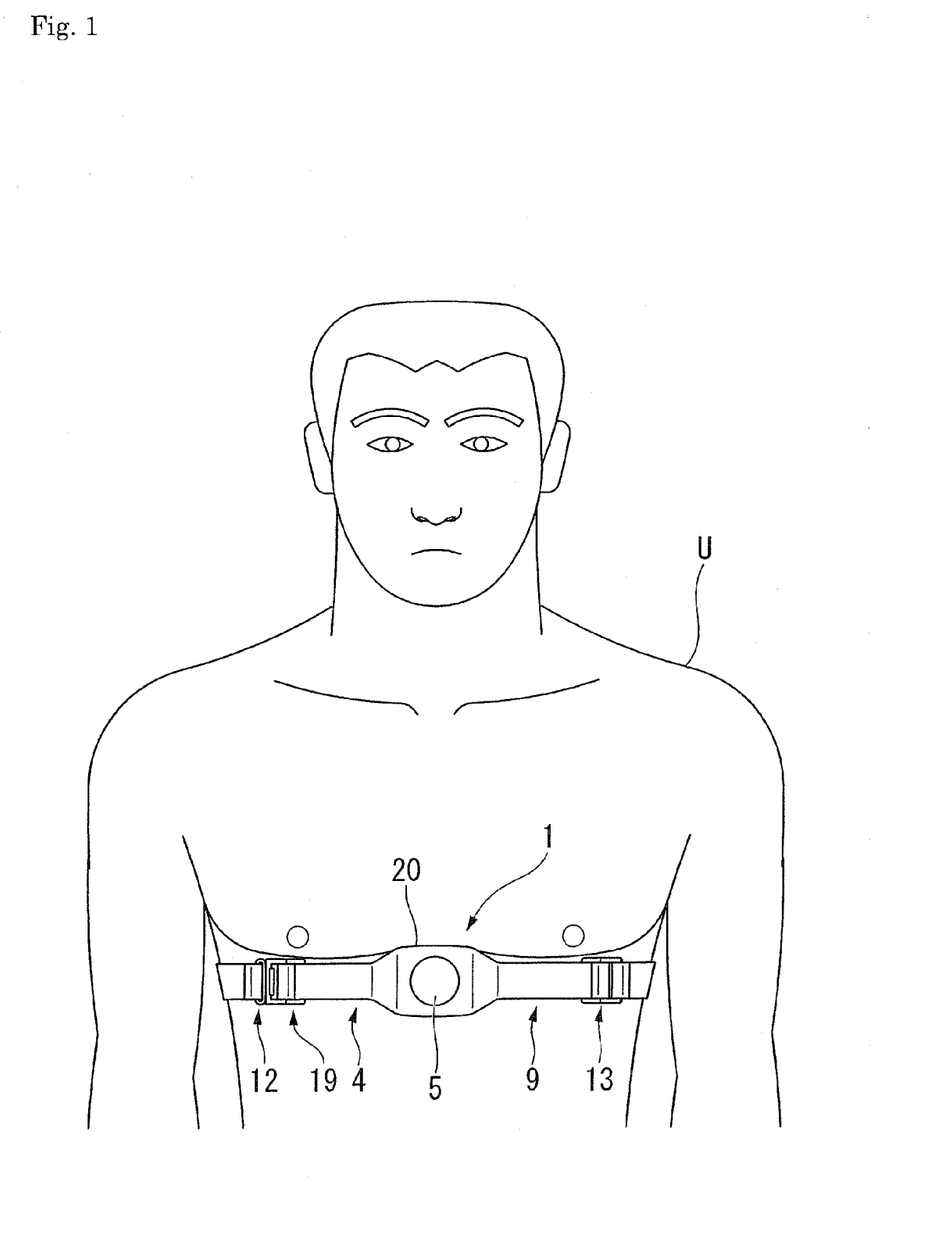
FIG. 1 is an explanatory diagram illustrating a state where a heartbeat measurement device according to a first embodiment of the present invention is installed on a user.
Figure 2:
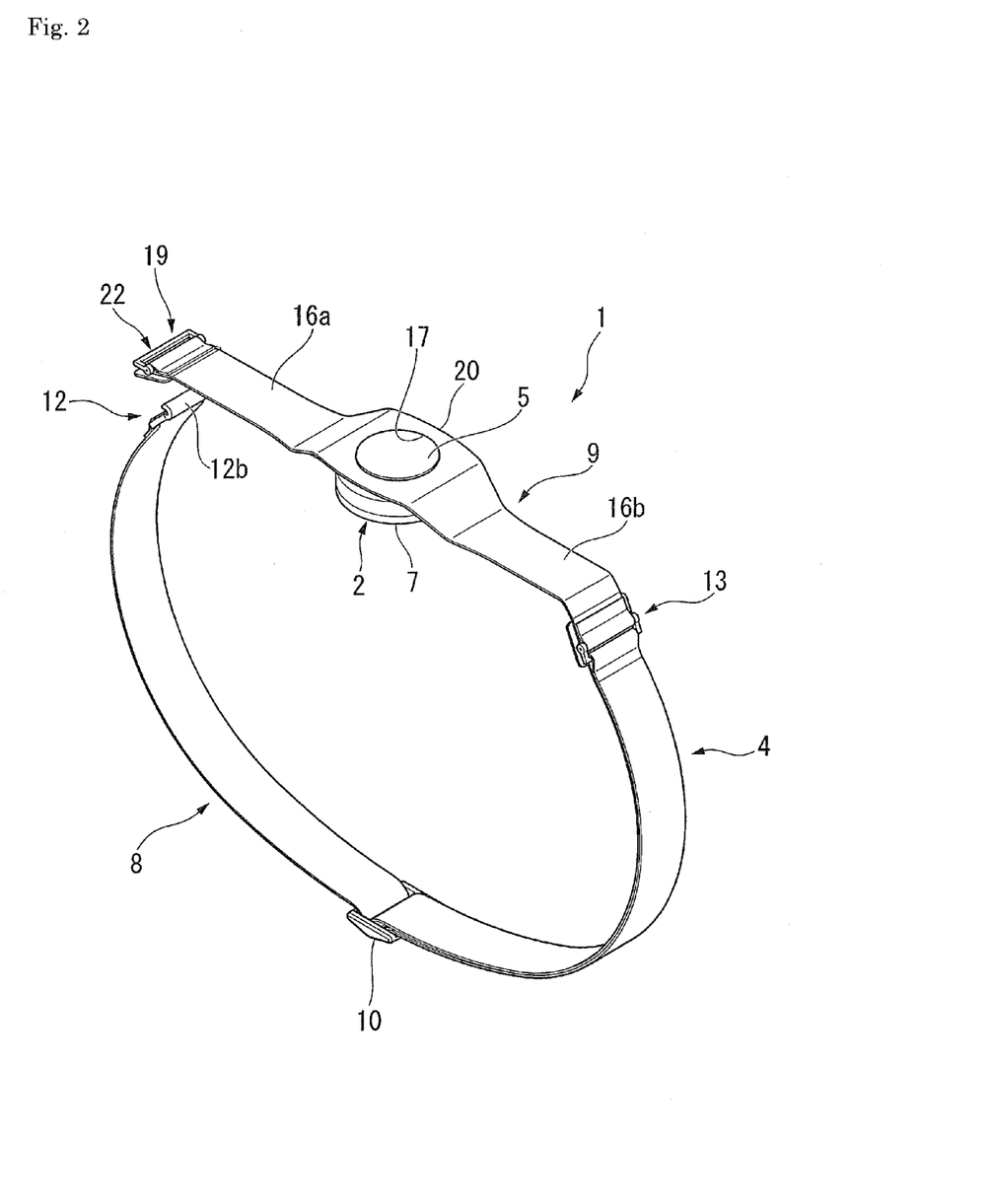
FIG. 2 is a perspective view illustrating the heartbeat measurement device according to the first embodiment of the present invention.
Figure 3:
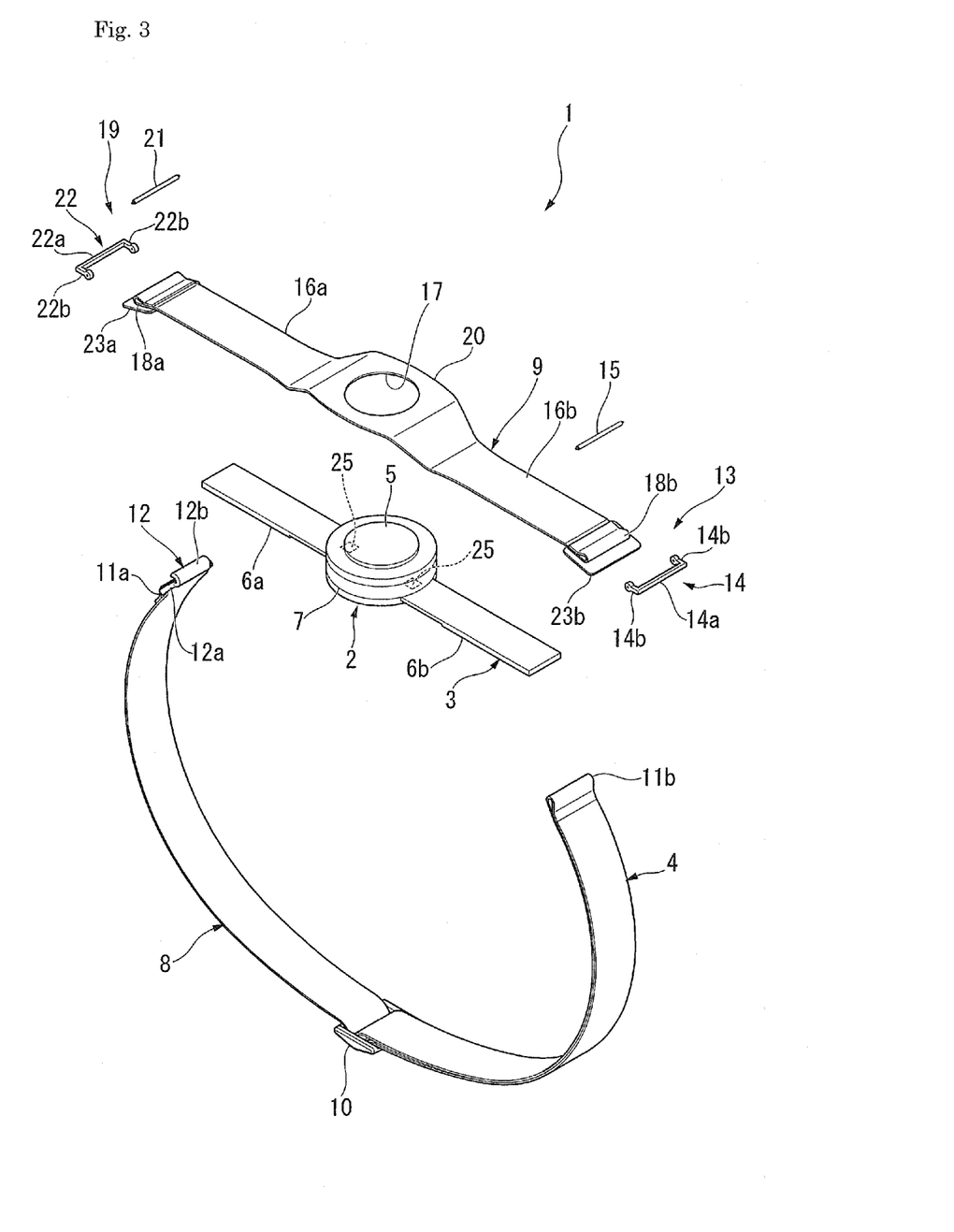
FIG. 3 is an exploded perspective view illustrating the heartbeat measurement device according to the first embodiment of the present invention.

FIG. 1 is an explanatory diagram illustrating a state where a heartbeat measurement device 1 which is a biological information detection device according to the present invention is installed on a user U, FIG. 2 is a perspective view illustrating the heartbeat measurement device 1, and FIG. 3 is an exploded perspective view illustrating the heartbeat measurement device 1.

As shown in FIGS. 1 to 3, the heartbeat measurement device 1 is mounted to the chest, which is a biological surface, of the user U to detect an electro-cardiac signal generated in association with heartbeat, and wirelessly communicates the detected electro-cardiac signal. The heartbeat measurement device 1 includes a main body portion 2, a heartbeat detection portion 3 formed integrally with the main body portion 2, and a fixing band 4 (fixing portion or mounting portion) for mounting the main body portion 2 and the heartbeat detection portion 3 to the chest of the user U.

The main body portion 2 includes a case 7 of which the external shape is formed in a substantially disk shape, and a detection circuit board (not shown) provided within the case 7. In the case 7, a fitting convex portion 5 is formed on the surface on the opposite side to the surface which comes into contact with the user U. The fitting convex portion 5 is to install the main body portion 2 on the fixing band 4.

Meanwhile, as the external shape of the case 7, various external shapes can be adopted without being limited to a substantial disk shape. For example, the external shape of the case 7 can also be formed in a rectangular plate shape.

A detection circuit board (not shown) includes a wireless transmission portion and a transmitter circuit (both not shown), and performs wireless communication on the basis of the signal detected by the heartbeat detection portion 3. The heartbeat detection portion 3 is electrically connected to the detection circuit board.

The heartbeat detection portion 3 is constituted by a pair of electrodes 6a and 6b. The electrodes 6a and 6b are made of a belt-like conductive elastomer, and one-side ends thereof in the long-side direction are connected to both sides with the main body portion 2 interposed therebetween. The electrodes 6a and 6b are electrically connected to the detection circuit board through an electrical connection portion 25 provided to the electrodes 6a and 6b and the detection circuit board (not shown) of the main body portion 2.

Meanwhile, as the conductive elastomer, for example, conductive silicon rubber mixed with carbon black, conductive rubber mixed with carbon black, conductive polyurethane rubber mixed with carbon black, or the like can be used.

(Fixing Band)

The fixing band 4 is formed in a substantially ring shape so as to be mounted over the whole circumference of the chest of the user U. More specifically, the fixing band 4 includes an elastic strap 8 having elasticity which is formed in a substantially belt shape, and a non-elastic belt 9 formed in a belt shape, and the belt 9 is connected thereto so as to be laid across both ends of the elastic strap 8 in the long-side direction.

A length adjustment member 10 for adjusting the length of the elastic strap 8 is provided substantially at the center of the elastic strap 8 in the long-side direction. In addition, ring portions 11a and 11b formed by folding back terminal portions of the elastic strap 8 are provided on both ends of the elastic strap 8 in the long-side direction.

A strap attaching and detaching member 12 capable of attaching and detaching the elastic strap 8 and the belt 9 is provided on one ring portion 11a out of the two ring portions 11a and 11b. The strap attaching and detaching member 12 is constituted by a shaft 12a inserted into the ring portion 11a, and a hook portion 12b provided so as to be laid across both ends of the shaft 12a.

In addition, a strap connector 13 for connecting the elastic strap 8 and the belt 9 is provided to the other ring portion 11b. The strap connector 13 is constituted by an approximately lateral U-shape connector body 14 when seen in plan view, and a shaft 15 engageable with the connector body 14.

The connector body 14 is configured such that a shaft portion 14a inserted into the ring portion 11b and a pair of arm portions 14b and 14b curvedly extended from both ends of the shaft portion 14a toward the belt 9 side are formed integrally with each other.

The shaft 15 extends so as to be laid across a pair of arm portions 14b and 14b. The tip of the shaft 15 is configured to freely come in and out, and to be in a state where it is biased toward the tip side by a spring (not shown). Thereby, the connector body 14 and the shaft 15 are engaged with each other.

On the other hand, the belt 9 is formed in a substantially belt shape by a fiber material so as to cover the main body portion 2 and the heartbeat detection portion 3 from the outside. The belt 9 is configured such that a holder portion 20 and a pair of band portions 16a and 16b extending toward both ends of the elastic strap 8 from both sides with the holder portion 20 interposed therebetween are formed integrally with each other. In the holder portion 20, a fitting hole 17 is formed in the central large portion. The internal diameter of the fitting hole 17 is set to be slightly smaller than the diameter of the fitting convex portion 5 of the main body portion 2. For this reason, when the fitting convex portion 5 of the main body portion 2 is pushed into the fitting hole 17, the fitting convex portion 5 is fitted and fixed into the fitting hole 17, and thus the main body portion 2 and the belt 9 are engaged with each other.

Ring portions 18a and 18b formed by folding back the terminal portions of the band portions 16a and 16b are provided on both ends of a pair of band portions 16a and 16b in the long-side direction. A strap engagement member 19 disengageable with the strap attaching and detaching member 12 of the elastic strap 8 is provided on one ring portion 18a out of the two ring portions 18a and 18b. The strap engagement member 19 is constituted by a shaft 21 inserted into the ring portion 18a and an engagement member body 22 provided so as to be laid across both ends of the shaft 21.

The engagement member body 22 is formed in an approximately lateral U-shape when seen in plan view, and is configured such that a shaft portion 22a and a pair of arm portions 22b and 22b curvedly extended from both ends of the shaft portion 22a toward the shaft 21 are formed integrally with each other. The shaft portion 22a is engageable with the hook portion 12b constituting the strap attaching and detaching member 12 of the elastic strap 8.

In addition, the shaft 15 of the strap connector 13 provided on the elastic strap 8 is inserted into the other ring portion 18b. Thereby, the elastic strap 8 and the belt 9 are connected to each other through the strap connector 13.

Herein, a belt-like human body protective portion 23a for preventing an exposure of the strap attaching and detaching member 12 and the strap engagement member 19 to the inner surface side, that is, an exposure to the side of the chest of the user U is installed on the ring portion 18a of the band portion 16b. In addition, a belt-like human body protective portion 23b for prevent an exposure to the side of the chest of the user U in the strap connector 13 is installed on the ring portion 18b of the band portion 16b.

In mounting the heartbeat measurement device 1 to the chest of the user U based on such a configuration, the main body portion 2 is first installed on the holder portion 20 constituting the belt 9 of the fixing band 4. Thereafter, the main body portion 2 and the heartbeat detection portion 3 are installed on the fixing band 4, and the main body portion 2 and the heartbeat detection portion 3 are positioned with respect to the fixing band 4. Herein, in installing the main body portion 2 on the holder portion 20, the installation thereof is performed by matching the long-side direction of the belt 9 with the long-side direction of the electrodes 6a and 6b of the heartbeat detection portion 3.

Subsequently, in a state (see FIG. 2) where the engagement of the strap attaching and detaching member 12 provided on the elastic strap 8 with the strap engagement member 19 provided on the belt 9 is released, the fixing band 4 is wound around the chest of the user U. At this time, the fixing band 4 is wound so that the main body portion 2 is located at the center of the chest of the user U (see FIG. 1). Thereafter, the hook portion 12b of the strap attaching and detaching member 12 and the engagement member body 22 of the strap engagement member 19 are caused to be engaged with each other. Thereby, the fixing band 4 is installed on the chest of the user U in such a way that the belt 9 covers the top of the main body portion 2 and the heartbeat detection portion 3, and the mounting of the heartbeat measurement device 1 to the user U is completed. That is, in a state where the fixing band 4 and the heartbeat detection portion 3 are separated from each other, the heartbeat detection portion 3 and the main body portion 2 are fixed to the user U. An electro-cardiac signal generated in association with heartbeat is detected by a pair of electrodes 6a and 6b. The detection circuit board (not shown) of the main body portion 2 wirelessly communicates the electro-cardiac signal detected by a pair of electrodes 6a and 6b.

At this time, since the human body protective portion 23a is provided on the area corresponding to the strap attaching and detaching member 12 of the fixing band 4 and the strap engagement member 19, and the human body protective portion 23b is provided on the area corresponding to the strap connector 13 of the fixing band 4, there is no case where the strap attaching and detaching member 12, the strap engagement member 19, and the strap connector 13 directly come into contact with the chest of the user U, and thus the user U feels no sense of discomfort.

Herein, although the belt 9 is formed in a substantially belt shape from a fiber material, a mesh or the like may be used. Thereby, moisture retention of the belt 9 increases, and thus conductivity thereof is improved. For this reason, the detection accuracy of the electrodes 6a and 6b increases.

In addition, since the elastic strap 8 of the fixing band 4 is elastic, the length of the entire fixing band 4 is set to be slightly shorter than the chest circumference of the user U by adjusting the length of the elastic strap 8. Thereby, the elastic strap 8 elongates slightly, and the adhesion of the fixing band 4 to the user U increases.

(Effect)

Therefore, according to the above-mentioned first embodiment, in a state where the main body portion 2 and the heartbeat detection portion 3 are formed integrally with each other, and the fixing band 4 and the heartbeat detection portion 3 are separated from each other using the fixing band 4, the heartbeat detection portion 3 and the main body portion 2 are fixed to the user U. Thus, the electrodes 6a and 6b are pressed and fixed to the band portions 16a and 16b, thereby allowing the heartbeat measurement device 1 to be reliably prevented from falling off while preventing external force in the tensile direction from being applied.

In addition, since the belt 9 on which the main body portion 2 is installed is formed from a fiber material and thus is non-elastic, the belt does not elongate. For this reason, the fitting hole 17 of the holder portion 20 into which the main body portion 2 is fitted and fixed is not deformed, and the main body portion 2 can be prevented from falling off the holder portion 20.

Further, since the belt 9 covers the top of the main body portion 2 and the heartbeat detection portion 3, the electrodes 6a and 6b are pressed by the band portions 16a and 16b. The electrodes 6a and 6b are formed from a conductive elastomer and thus are soft, and are pressed by the band portions 16a and 16b. Thereby, the electrodes are elastically deformed along the chest of the user U. For this reason, the electrodes 6a and 6b reliably adhere tightly to the chest of the user U.

Since the main body portion 2 and the heartbeat detection portion 3 can be separated from the fixing band 4 in a state where the main body portion 2 and the heartbeat detection portion 3 are formed integrally with each other, it is possible to easily clean only the fixing band 4. At this time, as in conventional cases, since the fixing band 4 is not provided with the electrodes 6a and 6b, it is possible to reliably prevent defects from occurring in electrical parts such as the electrodes 6a and 6b and the electrical connection portion 25. In this manner, the heartbeat measurement device 1 can secure good maintenance. Further, it is possible to reliably prevent defects from occurring in the electrical connection portion 25 for electrically connecting the detection circuit board (not shown) of the main body portion 2 to the electrodes 6a and 6b.

Meanwhile, in the above-mentioned first embodiment, a case has been described in which the main body portion 2 and the heartbeat detection portion 3 are installed on the fixing band 4 by fitting and fixing the fitting convex portion 5 of the main body portion 2 into the fitting hole 17 formed in the holder portion 20 of the belt 9, and the main body portion 2 and the heartbeat detection portion 3 are positioned with respect to the fixing band 4. However, without being limited thereto, one of the main body portion 2 and the belt 9 is provided with a positioning pin, and the other one is provided with a hole capable of inserting the positioning pin, so that the main body portion 2 may be installed on the fixing band 4, or the main body portion 2 and the heartbeat detection portion 3 may be positioned with respect to the fixing band 4.

In addition, in the above-mentioned first embodiment, a case has been described in which in mounting the heartbeat measurement device 1 to the chest of the user U, the main body portion 2 is first installed on the holder portion 20 of the fixing band 4, and then the fixing band 4 is wound around and fixed to the chest of the user U. However, without being limited thereto, the fixing band 4 may be wound around and fixed to the chest of the user U, and then the main body portion 2 may be installed on the holder portion 20 of the fixing band 4.

Second Embodiment

Next, a second embodiment of the present invention will be described with reference to FIGS. 4 and 5. Meanwhile, the same components as those of the first embodiment are designated by the same reference signs, and the description thereof will be made (the same is true of the following embodiment).

Figure 4:
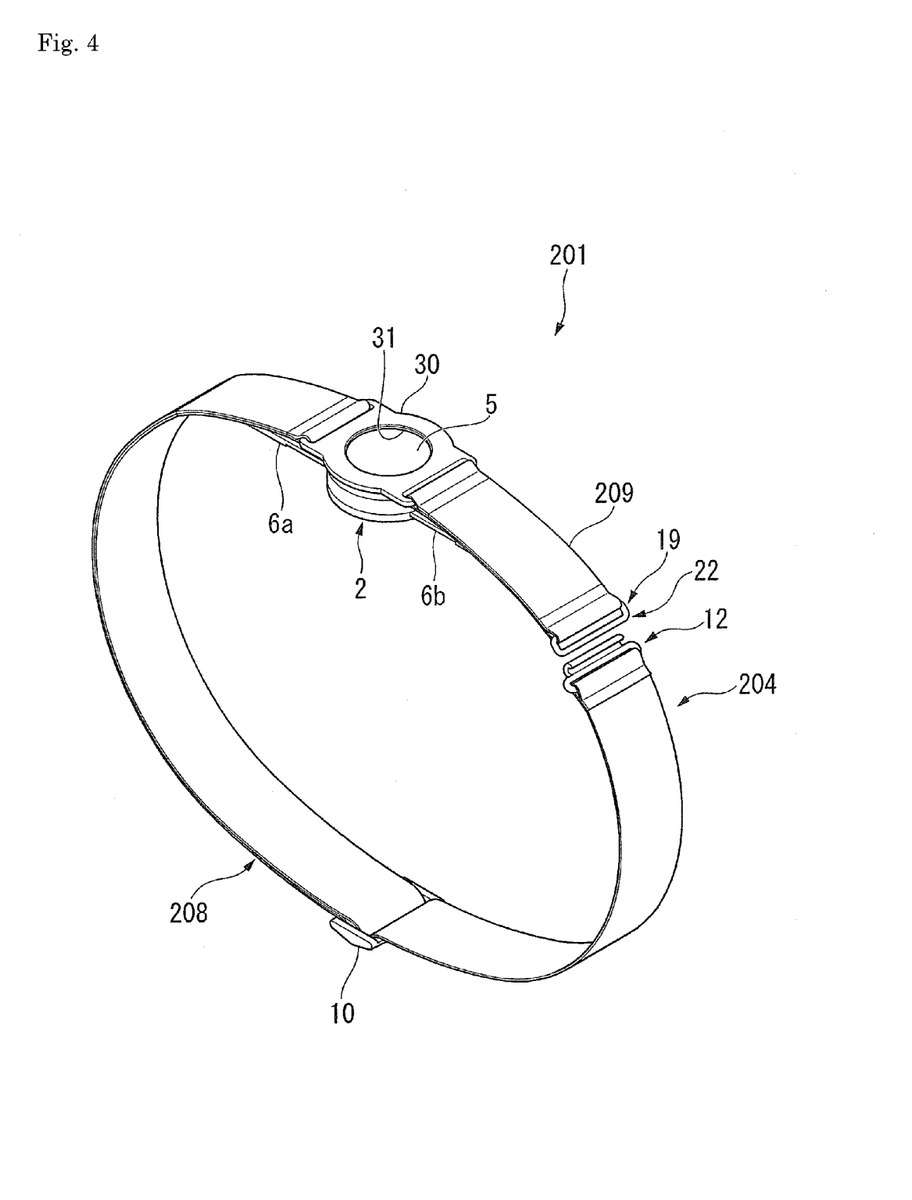
FIG. 4 is a perspective view illustrating a heartbeat measurement device according to a second embodiment of the present invention.
Figure 5:
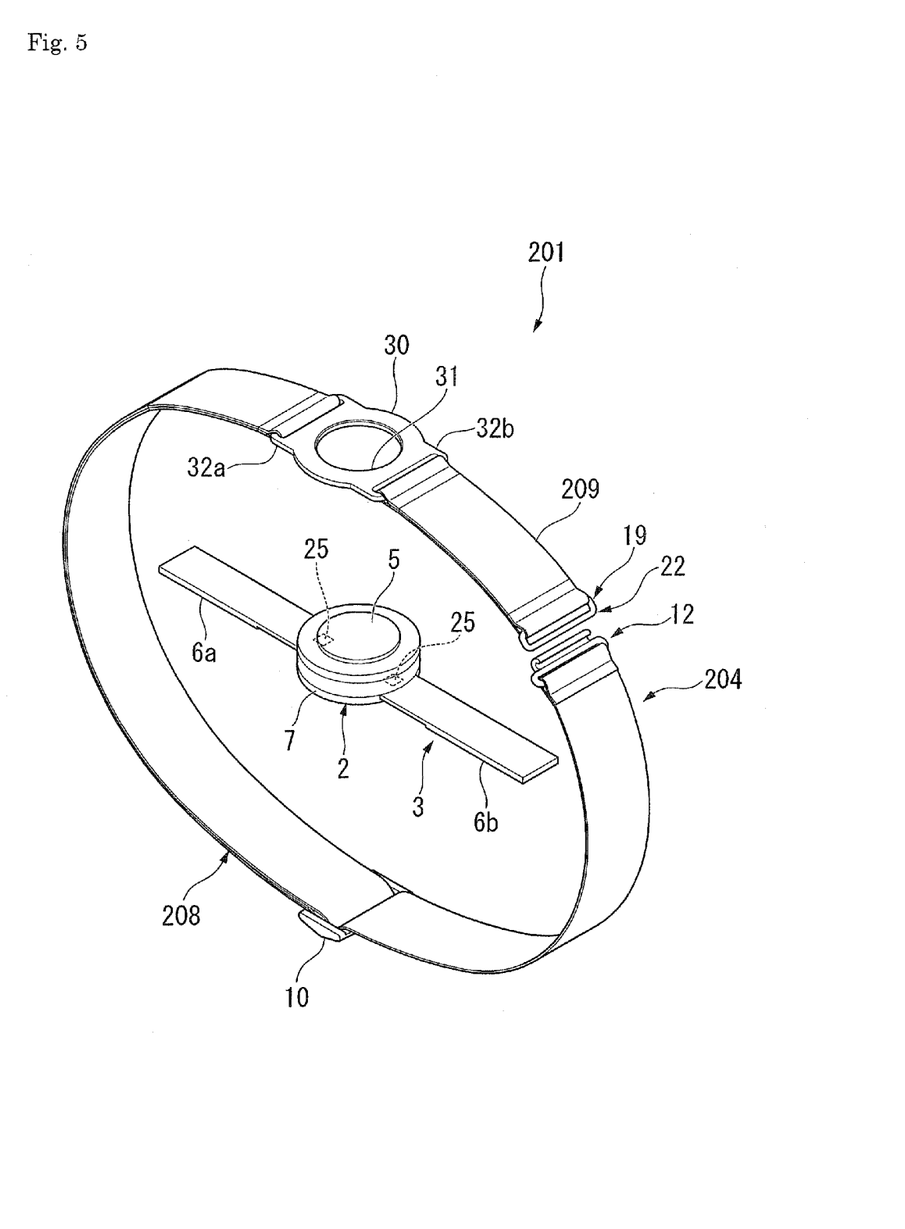
FIG. 5 is a perspective view illustrating the heartbeat measurement device in which a main body portion and a heartbeat detection portion are uninstalled from a fixing band according to the second embodiment of the present invention.

FIG. 4 is a perspective view illustrating a heartbeat measurement device 201 according to the second embodiment, and FIG. 5 is a perspective view illustrating the heartbeat measurement device 201 and shows a state where the main body portion 2 and the heartbeat detection portion 3 are uninstalled from the fixing band 204.

As shown in FIGS. 4 and 5, in the second embodiment, the heartbeat measurement device 201 includes the main body portion 2, the heartbeat detection portion 3 formed integrally with the main body portion 2, and the fixing band 204 for mounting the main body portion 2 and the heartbeat detection portion 3 to the chest of the user U. The following basic configuration of the embodiment is the same as that of the above-mentioned first embodiment (the same is true of the following embodiment): the heartbeat detection portion 3 and the fixing band 204 are separated from each other; the heartbeat detection portion 3 is constituted by a pair of electrodes 6a and 6b; the electrodes 6a and 6b is formed from a belt-like conductive elastomer, and one-side ends thereof in the long-side direction are connected to both sides with the main body portion 2 interposed therebetween; the electrodes 6a and 6b are electrically connected to the detection circuit board through the electrical connection portion 25 provided to the detection circuit board (not shown) of the main body portion 2, and the like.

(Fixing Band)

Herein, the difference between the second embodiment and the above-mentioned first embodiment is that the shapes of the fixing band 4 of the first embodiment and the fixing band 204 of the second embodiment are different from each other.

More specifically, the fixing band 204 is configured such that one end of an elastic strap 208, formed in a substantially belt shape, which has elasticity and one end of a non-elastic belt 209 formed in a belt shape are connected to each other through a connection member 30, and that the other end of the elastic strap 208 and the other end of the belt 209 are disengageable with each other through the strap attaching and detaching member 12 and the strap engagement member 19.

The connection member 30 is formed by a rigid member such as resin in a substantially circular-ring shape when seen in plan view, and a fitting hole 31 located at the central portion is formed therein. Meanwhile, the connection member 30 is not limited to the formation in a substantially circular-ring shape when seen in plan view, but may be formed in a ring shape. For example, the external shape thereof may be rectangular when seen in plan view. In this case, the shape of the fitting hole 31 may also correspond to the external shape of the connection member 30. Further, in this case, the shape of the fitting convex portion 5 also corresponds to that of the fitting hole 31.

Herein, the internal diameter of the fitting hole 31 is set to be slightly smaller than the diameter of the fitting convex portion 5 of the main body portion 2. In addition, a connection 32a capable of connecting one end of the elastic strap 208 and a connection 32b capable of connecting one end of the belt 209 are respectively formed on both sides with the fitting hole 31 of the connection member 30 interposed therebetween.

When the fitting convex portion 5 of the main body portion 2 is pushed into the fitting hole 31 formed in the connection member 30 based on such a configuration, the fitting convex portion 5 is fitted and fixed into the fitting hole 31. Thereby, the main body portion 2 and the heartbeat detection portion 3 are installed on the fixing band 204, and the main body portion 2 and the heartbeat detection portion 3 are positioned with respect to the fixing band 204.

In addition, when the fixing band 204 is wound so that the main body portion 2 is located at the center of the chest of the user U, the connection member 30 is formed by a rigid member such as resin, and thus deformation thereof is prevented.

Therefore, according to the above-mentioned second embodiment, it is possible to accomplish the same effect as that of the above-mentioned first embodiment.

Meanwhile, in the above-mentioned second embodiment, a case has been described in which the main body portion 2 and the heartbeat detection portion 3 are installed on the fixing band 204 by fitting and fixing the fitting convex portion 5 of the main body portion 2 into the fitting hole 31 formed in the connection member 30, and the main body portion 2 and the heartbeat detection portion 3 are positioned with respect to the fixing band 204. However, without being limited thereto, one of the main body portion 2 and the connection member 30 is provided with a positioning pin, and the other one is provided with a hole capable of inserting the positioning pin, so that the main body portion 2 may be installed on the fixing band 204, or the main body portion 2 and the heartbeat detection portion 3 may be positioned with respect to the fixing band 204.

In addition, in the above-mentioned second embodiment, a case has been described in which the belt 209 is formed in a belt shape and is non-elastic. However, the belt 209 may be elastic without being limited thereto.

Further, in the above-mentioned second embodiment, similarly to the above-mentioned first embodiment, the belt-like human body protective portion 23a (see FIG. 3) for preventing an exposure to the side of the chest of the user U may also be installed on the inner surface side of the strap engagement member 19 in the belt 209.

Third Embodiment

Next, a third embodiment of the present invention will be described with reference to FIGS. 6 and 7.

Figure 6:
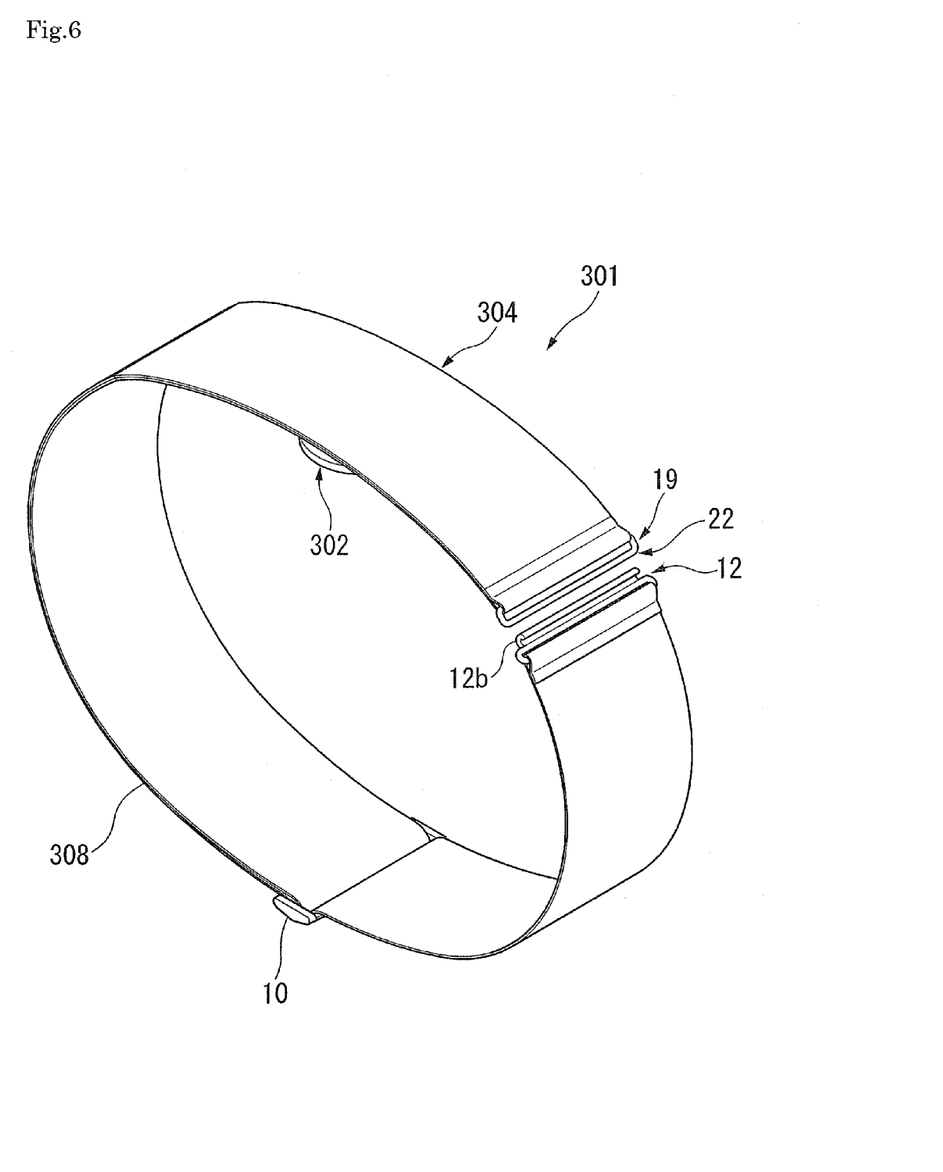
FIG. 6 is a perspective view illustrating a heartbeat measurement device according to a third embodiment of the present invention.
Figure 7:
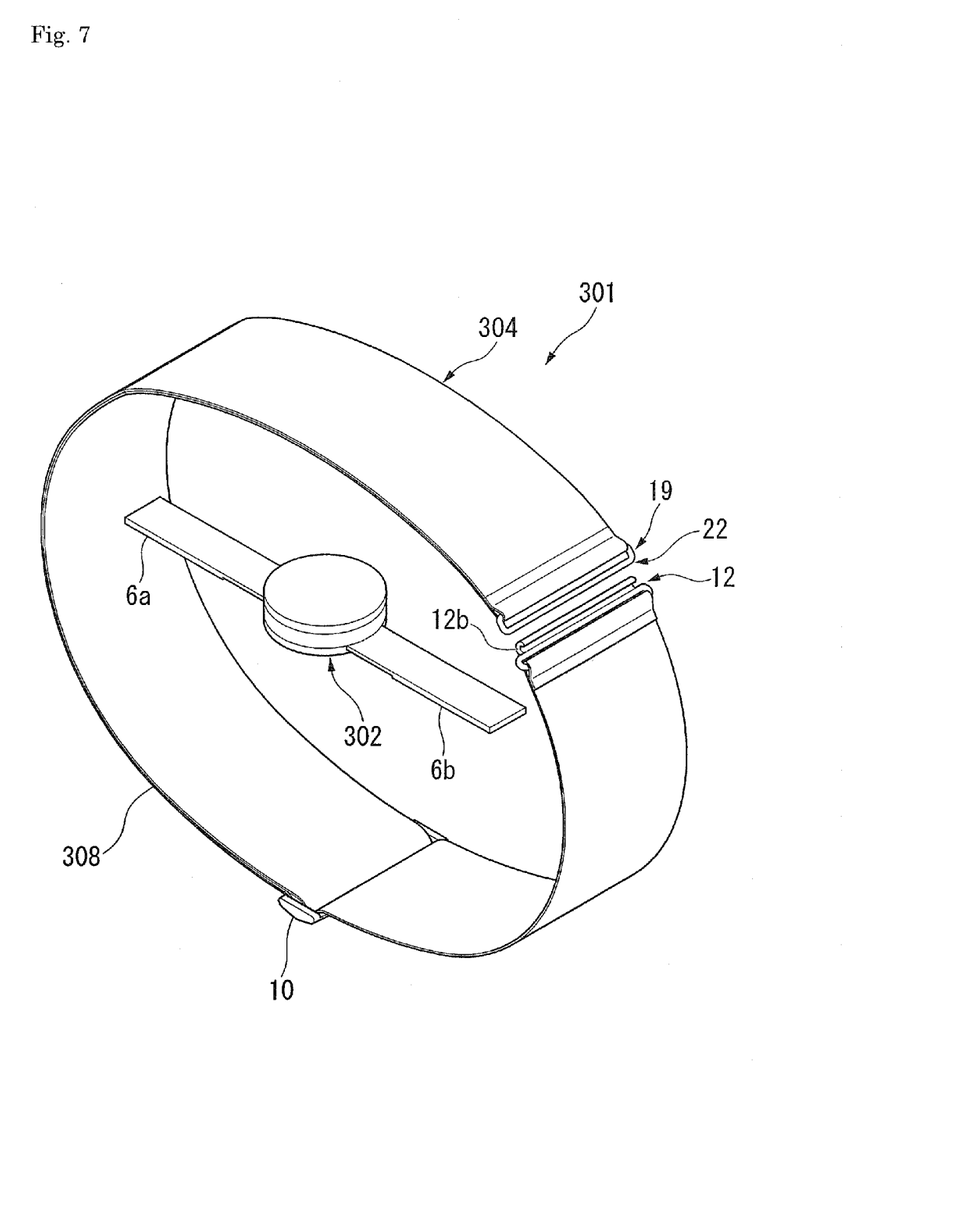
FIG. 7 is a perspective view illustrating the heartbeat measurement device in which a main body portion and a heartbeat detection portion are uninstalled from a fixing band according to the third embodiment of the present invention.

FIG. 6 is a perspective view illustrating a heartbeat measurement device 301 according to the third embodiment, and FIG. 7 is a perspective view illustrating the heartbeat measurement device 301, and shows a state where the main body portion 2 and the heartbeat detection portion 3 are uninstalled from a fixing band 304.

As shown in FIGS. 6 and 7, the difference between the third embodiment and the above-mentioned first embodiment is that the configurations of the fixing band 4 of the first embodiment and the fixing band 304 of the third embodiment are different from each other.

(Fixing Band)

More specifically, the fixing band 304 is configured such that both ends of an elastic strap 308, formed in a substantially belt shape, which has elasticity are disengageable with each other through the strap attaching and detaching member 12 and the strap engagement member 19. That is, the fixing band 304 of the third embodiment includes only the elastic strap 308 and does not include the non-elastic belt 9.

The elastic strap 308 is formed so as to be capable of covering the main body portion 2 and the heartbeat detection portion 3 from the upper side thereof. In addition, a fitting hole for installing a main body portion 302 is not formed in the elastic strap 308. For this reason, the fitting convex portion to be installed on the elastic strap 308 is not also formed in the main body portion 302.

In mounting the heartbeat measurement device 301 to the chest of the user U based on such a configuration, the main body portion 2 and the heartbeat detection portion 3 are placed on the chest of the user U, and then the fixing band 304 is wound around the chest of the user U so as to cover the main body portion 2 and the heartbeat detection portion 3. The strap attaching and detaching member 12 and the strap engagement member 19 which are provided on both ends of the elastic strap 308 are caused to be engaged with each other, and the mounting of the heartbeat measurement device 301 is completed.

Therefore, according to the above-mentioned third embodiment, in addition to the same effect as that of the above-mentioned first embodiment, it is possible to reduce product costs due to the simple structure.

Meanwhile, in the above-mentioned third embodiment, a case has been described in which in mounting the heartbeat measurement device 301 to the chest of the user U, the fixing band 304 is simply wound from the top of the main body portion 2 and the heartbeat detection portion 3. However, without being limited thereto, for example, a snap button may be provided in the inner surface of the elastic strap 308, and another snap button engageable with the snap button may be provided in a place corresponding to the snap button of the elastic strap 308 in the main body portion 302. According to such a configuration, it is possible to mount the heartbeat measurement device 301 to the chest of the user U in a state where the main body portion 2 is installed on the elastic strap 308, without forming a fitting hole in the elastic strap 308, or engaging the fitting convex portion with the main body portion 302.

In addition, in the above-mentioned third embodiment, a case has been described in which in mounting the heartbeat measurement device 301 to the chest of the user U, the main body portion 2 and the heartbeat detection portion 3 are placed on the chest of the user U, and then the fixing band 304 is wound around the chest of the user U so as to cover the main body portion 2 and the heartbeat detection portion 3. However, without being limited thereto, the fixing band 304 may be wound around the chest of the user U, and then the main body portion 2 and the heartbeat detection portion 3 may be placed on the inside of the fixing band 304.

Fourth Embodiment

Next, a fourth embodiment of the present invention will be described with reference to FIGS. 8 and 9.

Figure 8:
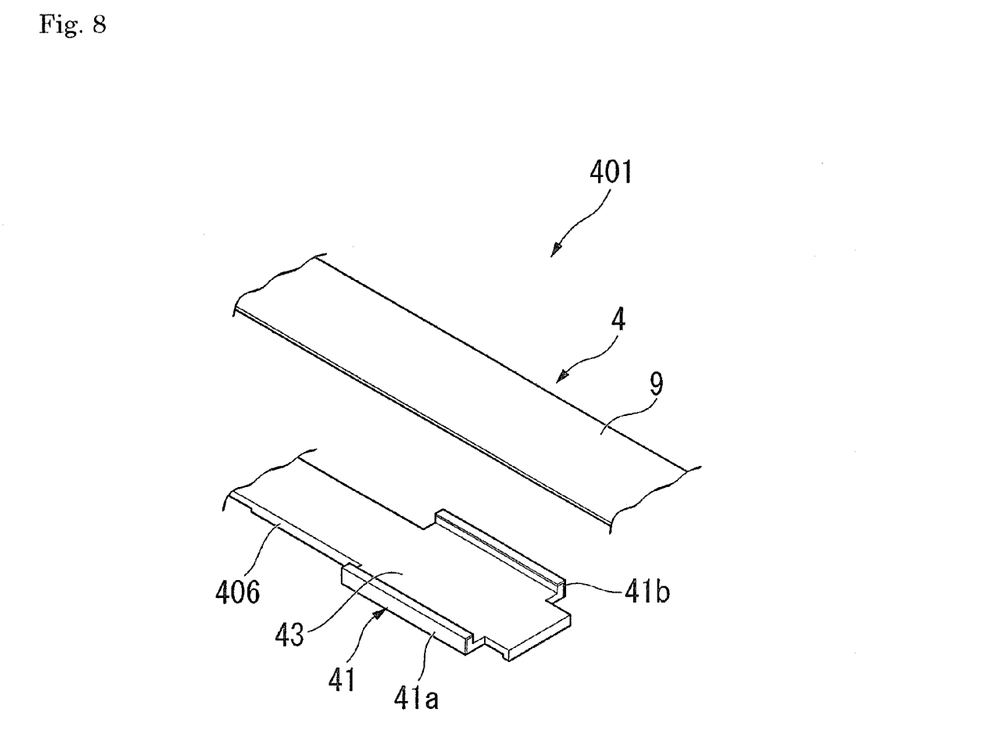
FIG. 8 is a perspective view illustrating the periphery of an electrode of a heartbeat measurement device according to a fourth embodiment of the present invention.
Figure 9:
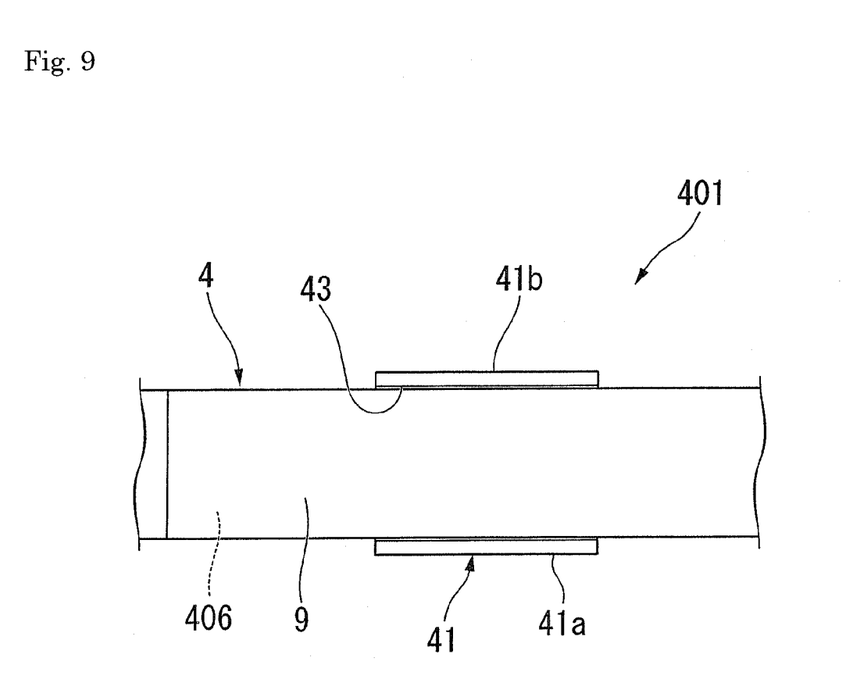
FIG. 9 is a top view illustrating the periphery of the electrode of the heartbeat measurement device according to the fourth embodiment of the present invention.

FIG. 8 is a perspective view illustrating the periphery of an electrode 406 of a heartbeat measurement device 401, and FIG. 9 is a top view illustrating the periphery of an electrode 406 of the heartbeat measurement device 401.

As shown in FIGS. 8 and 9, the difference between the fourth embodiment and the above-mentioned first embodiment is that a guide portion 41 for preventing displacement of the relative position between the electrode 406 and the belt 9 is formed in the electrode 406 of the fourth embodiment, while the guide portion 41 is not formed in the first embodiment.

(Guide)

More specifically, in the electrode 406, the guide portion 41 is formed at the other end side (right side in FIGS. 8 and 9) on the opposite side to the main body portion 2 (not shown in FIGS. 8 and 9). The guide portion 41 is constituted by two walls 41a and 41b formed upright from both sides of the electrode 406 in the short-side direction toward the belt 9 side. A receiving concave portion 43 capable of receiving the belt 9 is formed by the two walls 41a and 41b and the electrode 406.

When the main body portion 2 and the electrode 406 are installed on the fixing band 4 based on such a configuration, the belt 9 is received in the receiving concave portion 43 of the electrode 406. Then, displacement of the electrode 406 in the width direction with respect to the belt 9 is regulated by the wall 41a and 41b of the receiving concave portion 43. For this reason, the displacement of the relative position between the belt 9 and the electrode 406 is prevented.

Therefore, according to the above-mentioned fourth embodiment, in addition to the same effect as that of the above-mentioned first embodiment, the electrode 406 can be reliably caused to adhere tightly to the chest of the user U, and thus it is possible to improve measurement accuracy of the heartbeat measurement device 401.

Meanwhile, two walls 41a and 41b are exposed from both sides of the belt 9 in the short-side direction in a state where the main body portion 2 and the electrode 406 are installed on the fixing band 4. For this reason, in order to prevent a pair of electrodes 406 from being short-circuited through clothes or the like, it is preferable to perform an insulation process such as application of an insulating coating to the walls 41a and 41b. Herein, an insulation processing method is not limited to insulating coating.

In addition, the guide portion 41 of the fourth embodiment can also be applied to the elastic strap 308 of the above-mentioned third embodiment. According to such a configuration, it is possible to prevent the displacement of the heartbeat detection portion 3.

Fifth Embodiment

Next, a fifth embodiment of the present invention will be described with reference to FIGS. 10 and 11.

Figure 10:
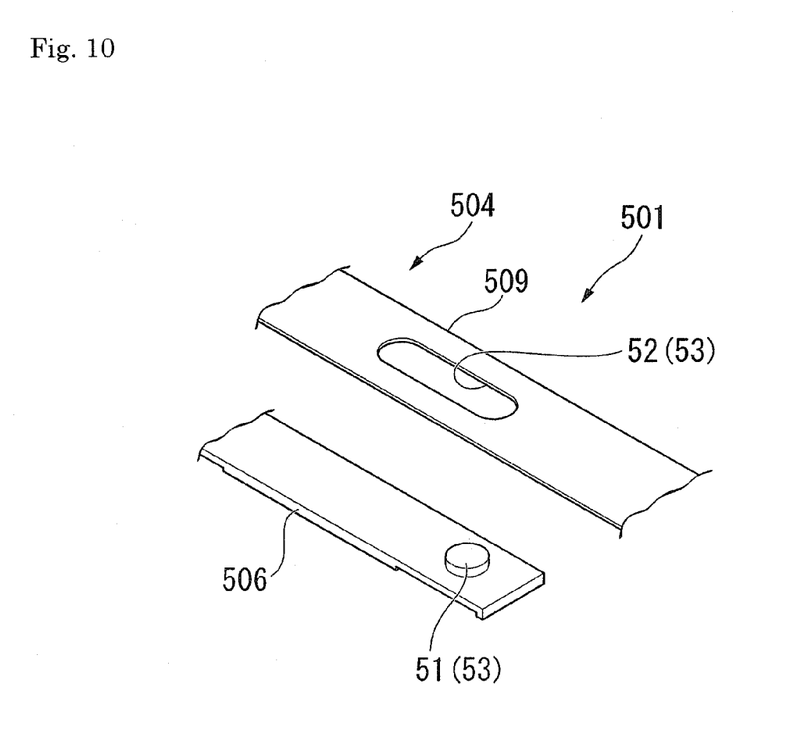
FIG. 10 is a perspective view illustrating the periphery of an electrode of a heartbeat measurement device according to a fifth embodiment of the present invention.
Figure 11:
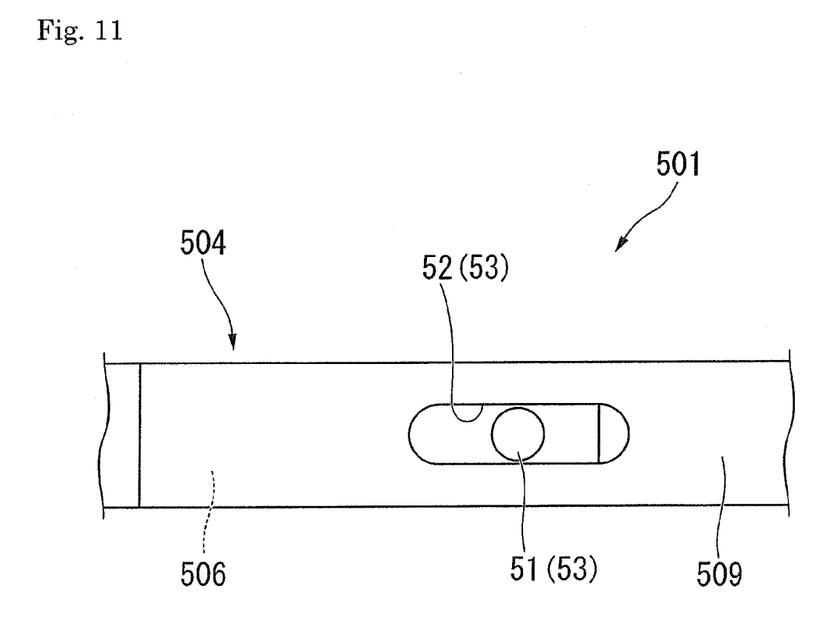
FIG. 11 is a top view illustrating the periphery of the electrode of the heartbeat measurement device according to the fifth embodiment of the present invention.

FIG. 10 is a perspective view illustrating the periphery of an electrode 506 of a heartbeat measurement device 501, and FIG. 11 is a top view illustrating the periphery of the electrode 506 of the heartbeat measurement device 501.

As shown in FIGS. 10 and 11, the difference between the fifth embodiment and the above-mentioned first embodiment is that a displacement prevention portion 53 for preventing displacement of the relative position between each other is provided to the electrode 506 and a belt 509 of the fifth embodiment, while the displacement prevention portion is not provided in the first embodiment.

(Displacement Prevention Portion)

The displacement prevention portion 53 will be described in more detail below.

In the electrode 506, a convex portion 51 is formed at the other end side (right side in FIGS. 10 and 11) on the opposite side to main body portion 2 (not shown in FIGS. 10 and 11) to protrude toward the belt 509 side. On the other hand, in the belt 509, a long hole portion 52 capable of inserting the convex portion 51 is formed in a place corresponding to the convex portion 51. The long hole portion 52 is formed in an elliptical shape along the long-side direction of the belt 509.

When the main body portion 2 and the electrode 506 are installed on the fixing band 504 based on such a configuration, the convex portion 51 of the electrode 506 is inserted into the long hole portion 52 of the belt 509. Thereby, the displacement of the electrode 506 in the width direction with respect to the belt 509 is regulated, that is, the displacement of the relative position between the belt 509 and the electrode 506 is prevented.

Therefore, according to the above-mentioned fifth embodiment, it is possible to accomplish the same effect as that of the above-mentioned fourth embodiment.

Meanwhile, the convex portion 51 of the electrode 506 is exposed to the outside through the long hole portion 52 of the belt 509 in a state where the main body portion 2 and the electrode 506 are installed on the fixing band 504. For this reason, in order to prevent a pair of electrodes 506 from being short-circuited through clothes or the like, it is preferable to perform an insulation process such as application of an insulating coating to the convex portion 51. Herein, an insulation processing method is not limited to insulating coating. For example, the convex portion 51 may be formed by a separate member from the electrode 506, that is, an insulating member, and may be installed on the electrode 506. In addition, the electrode 506 and the convex portion 51 can also be formed by two-color molding.

In addition, the present invention is not limited to the above-mentioned embodiments, and various changes may be added to the above-mentioned embodiments without departing from the scope of the present invention.

For example, in the above-mentioned fourth embodiment, a case has been described in which the electrode 406 is provided with the guide portion 41, and the displacement of the relative position between the belt 9 and the electrode 406 is prevented. In the above-mentioned fifth embodiment, a case has been described in which the convex portion 51 is protrusively formed in the electrode 506, the long hole portion 52 capable of inserting the convex portion 51 is formed in the belt 509, and the displacement of the relative position between the belt 509 and the electrode 506 is prevented. However, a structure in which the displacement of the relative position between the belt 9 and the electrode 406 or the relative position between the belt 509 and the electrode 506 is capable of being prevented may be formed, without being limited thereto.

For example, each of the belts 9 and 509 and the electrodes 406 and 506 may be provided with a hook and loop fastener, and the displacement of the relative position between each other may be prevented. Meanwhile, a hook and loop fasteners may be installed on the belt 9 and the electrodes 6a and 6b in the above-mentioned first embodiment, the elastic strap 208, the belt 209, and the electrodes 6a and 6b in the second embodiment, or the elastic strap 308 and electrodes 6a and 6b in the third embodiment, and the displacement of the relative position between each other may be prevented.

In addition, in the above-mentioned embodiments, a case has been described in which the main body portions 2 and 302 and the heartbeat detection portion 3 are formed integrally with each other in the heartbeat measurement devices 1, 201, 301, 401, and 501 which measure a heart rate of the user U as the biological information detection devices, and the main body portions 2 and 302 and the heartbeat detection portion 3 are installed on the chest of the user U using the fixing bands 4, 204, 304, and 504. However, these configurations are not only applied to the heartbeat measurement devices 1, 201, 301, 401, and 501, but are also capable of being applied to various biological information detection devices. For example, as the biological information detection devices, the configurations of the above-mentioned embodiments can be applied to devices that measure blood pressure, body temperature, myogenic potential and the like.

What is claimed is:

1. A biological information detection device comprising:
a device main body having a convex portion and a detection circuit board;
a biological signal detection portion formed integrally with the device main body, the biological signal detection portion having at least one electrode for contacting a biological surface of a human body, the at least one electrode being electrically connected to the detection circuit board; and
a fixing portion for mounting the device main body and the biological signal detection portion to a human body, the fixing portion having an elastic strap and having a fitting hole into which the convex portion of the device main body is configured to be fitted and fixed so that the device main body and the biological signal detection portion are mounted to the human body without the device main body and the biological signal detection portion being directly attached to the elastic strap, the fixing portion covering the device main body and the biological signal detection portion with the electrode being disposed in contact with the biological surface of the human body when the device main body and the biological signal detection portion are mounted to the human body.

2. The biological information detection device according to claim 1, wherein the device main body is detachably provided to the fixing portion.

3. The biological information detection device according to claim 2, wherein the fixing portion has a non-elastic belt that is connected to the elastic strap and that is provided with the fitting hole, the device main body being detachably mounted to the non-elastic belt when the convex portion is fitted into the fitting hole.

4. The biological information detection device according to claim 2, wherein the fixing portion has a rigid connection member connected to the elastic strap, the device main body being detachably mounted to the rigid connection member.

5. The biological information detection device according to claim 1, wherein the biological signal detection portion is formed of a conductive elastomer serving as the electrode.

6. The biological information detection device according to claim 1, wherein the device main body has a first surface for contacting the biological surface of the human body, and a second surface opposite the first surface, the convex portion being formed on the second surface; and wherein the fixing portion has a non-elastic belt configured for detachable connection to the elastic strap, the non-elastic belt having fitting hole into which the convex portion of the device main body is configured to be fitted so that the device main body and the non-elastic belt are detachably engaged with one another.

7. The biological information detection device according to claim 1, wherein the device main body has a first surface for contacting the biological surface of the human body, and a second surface opposite the first surface, the convex portion being formed on the second surface; and wherein the fixing portion has a rigid connecting member configured for detachable connection to the elastic strap, the rigid connecting member having the fitting hole into which the convex portion of the device main body is configured to be fitted so that the device main body and the rigid connecting member are detachably engaged with one another.

8. The biological information detection device according to claim 1, wherein the fixing portion has a non-elastic belt configured for detachable connection to the elastic strap, the non-elastic belt having a pair of band portions for detachable connection to the elastic strap and a holder portion disposed between the pair of band portions and having the fitting hole, the holder portion being configured for detachable connection to the device main body when the convex portion of the device main body is fitted in the fitting hole.

9. A biological information detection device comprising:
a device main body having a convex portion
a biological signal detection portion formed integrally with the device main body, the biological signal detection portion having a pair of electrodes for contacting a biological surface of a human body; and
a fixing portion for mounting the device main body and the biological signal detection portion to a human body, the fixing portion having an elastic strap and having a fitting hole into which the convex portion of the device main body is configured to be fitted and fixed so that the device main body and the biological signal detection portion are mounted to the human body without the device main body and the biological signal detection portion being directly attached to the elastic strap, the fixing portion covering the device main body and the biological signal detection portion with the electrodes being disposed in contact with the biological surface of the human body when the device main body and the biological signal detection portion are mounted to the human body,
wherein the fixing portion has a non-elastic belt configured for detachable connection to the elastic strap, the non-elastic belt having a pair of band portions for detachable connection to the elastic strap and a holder portion disposed between the pair of band portions and having the fitting hole, the holder portion being configured for detachable connection to the device main body when the convex portion of the device main body is fitted in the fitting hole, and
wherein the pair of electrodes extend from opposite sides of the device main body, the pair of electrodes being configured to be disposed in overlapping relation with the respective pair of band portions when the holder portion and the device main body are detachably connected to one another.

10. A biological information detection device comprising:
a main body portion having a convex portion and a detection circuit board;
a biological signal detection portion integral with the main body portion and having at least one electrode for detecting a biological signal of a human body, the at least one electrode being electrically connected to the detection circuit board; and
a mounting portion for mounting the main body portion and the biological signal detection portion to a human body to detect a biological signal of the human body, the mounting portion having an elastic strap and having a fitting hole into which the convex portion of the main body portion is configured to be fitted and fixed so that the main body portion and the biological signal detection portion are mounted to the human body without direct attachment of the elastic strap to the main body portion and the biological signal detection portion.

11. The biological information detection device according to claim 10, wherein the mounting portion has a non-elastic belt provided with the fitting hole, the non-elastic belt being configured for direct detachable connection to the elastic strap and configured for direct detachable connection to the main body portion when the convex portion is fitted into the fitting hole.

12. The biological information detection device according to claim 11, wherein the main body portion has a first surface for contacting the body and a second surface opposite the first surface, the convex portion being formed on the second surface; and wherein the non-elastic belt of the mounting portion has the fitting hole into which the convex portion is configured to be fitted so that the main body portion and the non-elastic belt are detachably connected to one another.

13. The biological information detection device according to claim 10, wherein the mounting portion has a rigid connecting member configured for direct detachable connection to the elastic strap and to the main body portion.

14. The biological information detection device according to claim 13, wherein the main body portion has a first surface for contacting the human body and a second surface opposite the first surface, the convex portion being formed on the second surface; and wherein the rigid connecting member of the mounting portion has a the fitting hole into which the convex portion is configured to be fitted so that the main body portion and the rigid connecting member are detachably connected to one another.

15. The biological information detection device according to claim 10, wherein the biological signal detection portion is formed of a conductive elastomer serving as the at least one electrode.

16. A biological information detection device comprising:
a main body portion having a convex portion;
a biological signal detection portion integral with the main body portion and having a pair of electrodes extending from opposite sides of the main body portion for detecting a biological signal of a human body; and a mounting portion for mounting the main body portion and the biological signal detection portion to a human body to detect a biological signal of the human body, the mounting portion having an elastic strap and having a fitting hole into which the convex portion of the main body portion is configured to be fitted and fixed so that the main body portion and the biological signal detection portion are mounted to the human body without direct attachment of the elastic strap to the main body portion and the biological signal detection portion, the mounting portion having a non-elastic belt for detachable connection to the elastic strap, the non-elastic belt having a holder portion for holding the main body portion and a pair of band portions configured to overlap the respective pair of electrodes when the main body portion and the biological signal detection portion are mounted to the human body, the holder portion having the fitting hole into which the convex portion of the main body portion is configured to be fitted.

17. The biological information detection device according to claim 16, wherein the biological signal detection portion is formed of a conductive elastomer serving as the pair of electrodes.

18. A biological information detection device comprising:
a device main body having a case, a detection circuit board provided within the case, a first surface configured to come into contact with a user, a second surface opposite the first surface, and a convex portion formed on the second surface;
a biological signal detection portion integral with the device main body for detecting a biological signal of the user when the first surface of the device main body contacts the user, the biological signal detection portion having a pair of electrodes connected to the detection circuit board of the device main body and extending from respective opposite sides of the case; and
a fixing band for mounting the device main body and the biological signal detection portion to a user for detection of a biological signal of the user, the fixing band having an elastic strap and a non-elastic belt configured for removable connection to the elastic strap, the non-elastic belt having a holder portion provided with a fitting hole into which the convex portion of the device main body is configured to be fitted and fixed to securely engage the device main body and the non-elastic belt with one another.

* * * * *